(12) United States Patent
Haugland et al.

(10) Patent No.: US 7,996,089 B2
(45) Date of Patent: *Aug. 9, 2011

(54) METHODS AND IMPLANTABLE SYSTEMS FOR NEURAL SENSING AND NERVE STIMULATION

(75) Inventors: Morten Haugland, Aalborg (DK); Thomas Sinkjaer, Svenstrup (DK)

(73) Assignee: Neurodan A/S, Aalborg (DK)

( * ) Notice: Subject to any disclaimer, the term of this patent is extended or adjusted under 35 U.S.C. 154(b) by 545 days.

This patent is subject to a terminal disclaimer.

(21) Appl. No.: 12/028,404

(22) Filed: Feb. 8, 2008

(65) Prior Publication Data

US 2008/0234782 A1  Sep. 25, 2008

Related U.S. Application Data

(63) Continuation-in-part of application No. 10/203,908, filed as application No. PCT/DK01/00112 on Feb. 16, 2001, now Pat. No. 7,403,821.

(30) Foreign Application Priority Data

Feb. 17, 2000  (DK) ................................ 2000 00191

(51) Int. Cl.
*A61N 1/36* (2006.01)

(52) U.S. Cl. ........................................................ 607/48

(58) Field of Classification Search ................... 607/46, 607/48

See application file for complete search history.

(56) References Cited

U.S. PATENT DOCUMENTS

| | | | |
|---|---|---|---|
| 4,750,499 A | 6/1988 | Hoffer | |
| 4,920,979 A * | 5/1990 | Bullara | 607/118 |
| 4,934,368 A | 6/1990 | Luch | |
| 5,470,341 A * | 11/1995 | Kuehn et al. | 607/5 |
| 5,748,845 A | 5/1998 | Labun | |
| 5,814,092 A | 9/1998 | King | |
| 5,814,093 A | 9/1998 | Stein | |
| 5,861,017 A | 1/1999 | Smith | |
| 6,315,721 B2 | 11/2001 | Schulman | |

(Continued)

FOREIGN PATENT DOCUMENTS

WO  97/37720  3/1997

(Continued)

OTHER PUBLICATIONS

Haugland et al., "Cutaneous Whole Nereve Recordings Used for Correction of Footdrop in Hemiplegic Man", IEEE Transactions on Rehabilitation Engineering, vol. 3, No. 4, Dec. 1995, pp. 307-317.*

(Continued)

*Primary Examiner* — Niketa I Patel
*Assistant Examiner* — Alyssa M Alter
(74) *Attorney, Agent, or Firm* — Pillsbury Winthrop Shaw Pittman LLP

(57) ABSTRACT

Apparatus for producing a dorsiflexion of the foot of a patient comprises a combined sensing and stimulation electrode device having neurosense and stimulation electrode means capable of sensing a nerve signal from a peripheral nerve and stimulating peripheral motor nerve fibers. The neurosense and stimulation electrode means are implantable above the knee of a patient. Means for receiving and processing the sensed nerve signals are provided to identify a signal indicative of the timing of hell strike and heel lift of the patient and for producing a control signal in response thereto. Means for operating said neurosense and stimulation electrode means in response to the control signal to produce stimulation of the peripheral motor nerve fibers are also provided.

24 Claims, 11 Drawing Sheets

U.S. PATENT DOCUMENTS 7,403,821 B2 * 7/2008 Haugland et al. ............... 607/49

FOREIGN PATENT DOCUMENTS

WO 00/15293 9/1999

OTHER PUBLICATIONS

Liberson et al., "Functional Electrotherapy: Stimulation of the Peroneal Nerve Synchronized with the Swing Phase of the Gait of Hemiplegic Patients," 1961, pp. 101-105.

Jeglič, et al., "Implantable Muscle/Nerve Stimulator as a Part of an Electronic Brace," 1970, pp. 593-603.

Waters, et al., "Experimental Correction of Footdrop by Electrical Stimulation of the Peroneal Nerve," 1975, pp. 1047-1054.

Waters, et al., "Functional Electrical Stimulation of the Peroneal Nerve for Hemiplegia," 1985, pp. 792-793.

Kelih, et al., Dual Channel Implantable Stimulator, 1988, pp. 127-130.

Symons., Trigger Switches for Implantable Gait Stimulation, 1986, pp. 319-321.

Haugland et al., IEEE Transactions on Rehabilitation Engineering, vol. 3, No. 4, Dec. 1995, pp. 307-317.

"Interfacing the body's own sensing receptors into neural prosthesis devices", Morten Haugland and Thomas Sinkjaer, Technology and Health Care 7 (1999) 393-399.

"Wireless Control of Functional Electricla Stimulation Systems", Z. Matjecic, M. Munih, T. Bajd, A. Kralj, H. Benko and P. Obreza, Articifial Organs 21 (3) 197-200.

Waters, et al., "Functional Electrical Stimulation of the Peroneal Nerve for Hemiplegia," 1985, pp. 792-793.

Symons., Trigger Switches for Implantable Gait Stimulation, 1986, pp. 319-321.

Stedman's Online Medical dictionary, www.stedmans.com, defined: glabrous.

Gray, Henry. The Complete Gray's Anatomy. Merchant Book Company Limited, British Sixteenth Edition, 2003.

Willemsen et al., IEEE Transactions on Biomedical Engineering, vol. 37, No. 1 2, Dec. 1990, pp. 1201-1208.

Haugland et al., "Cutaneous Whole Nerve Recordings Used for Correction of Footdrop in Hemiplegic Man"; IEEE Transactions on Rehabilitation Engineering; vol. 3, No. 4, Dec. 1995; pp. 307-317.

Upshaw et al.; "Digital Signal Processing Algorithms for the Detection of Afferent Nerve Activity Recorded from Cuff Electrodes"; IEEE Transactions on Rehabilitation Engineering; vol. 6, No. 2; Jun. 1998; pp. 172-181.

Kostov et al; "Machine Learning in Control of Functional Electrical Stimulation Systems for Locomotion"; IEEE Transaction on Biomedical Engineering; vol. 42, No. 6; Jun. 1995; pp. 541-551.

* cited by examiner

METHODS AND IMPLANTABLE SYSTEMS FOR NEURAL SENSING AND NERVE STIMULATION

CROSS REFERENCE TO RELATED APPLICATIONS

This application is a continuation-in-part of U.S. patent application Ser. No. 10/203,908, filed Nov. 15, 2002, now U.S. Pat. No. 7,403,821 which is the national stage of PCT/DK01/00112, filed Feb. 16, 2001, which in turn claims priority to Danish application no. PA 2000 00191 filed Feb. 17, 2000, the entire contents of all of which are incorporated herein in their entirety by reference.

FIELD OF THE INVENTION

The present invention relates in its broadest concept to methods and systems for electrically sensing signals originating from biological tissue and for the subsequent selective stimulation of muscular or neural tissue, the systems being at least partially implantable. More specifically, the present invention relates to the detection of neural or muscular activity, analysis of the signals and the subsequent stimulating of neural or muscular tissue based thereon. In a specific aspect, the invention relates to correction of foot drop based on these principles.

BACKGROUND OF THE INVENTION

Numerous conditions exist for the human body in which a disease or bodily malfunction have its origin in impaired function of the neuromuscular system, including deficiencies based upon impaired sensory as well as motor activity. In the following the problems addressed by the pre-sent invention will be discussed on the basis of the condition known as hemiplegic drop foot, a condition in which a patient is not able to lift, i.e. dorsiflex, the foot during gait, normally based on an Upper Motor Neurone Lesion (UMNL), for which stroke and head-injuries are by far the more prevalent problems with reported prevelances of 12,000/million for stroke and 20,000/million for head injuries.

Quite often persons who suffer a stroke recover a large amount of function following a period of treatment, but a persistent, long-term disability in approximately 10 to 20% of stroke survivors is UpperMotorNeurone-Drop Foot (UMN-DF). UMN-DF typically involves an inability to dorsiflex the foot during the swing phase of gait (Drop Foot), as well as loss of normal hip and knee flexion, and inability to 'push-off' as well as spasticity of the calf muscle group.

An important feature of UMNLs is that electrical excitability of the associated peripheral nerves is still intact, thus facilitating the use of Functional Electrical Stimulation (FES) to restore or enhance gait for some of these cases. As early as in 1961, Liberson and his co-workers proposed application of electrical stimulation (ES) to the common peroneal nerve to correct this condition and using a foot-switch synchronised the application of ES to the swing phase of gait, using a device subsequently referred to as a Peroneal Stimulator (PS) or Drop Foot Stimulator (DFS) [Liberson, W. T., Holmquest, H. J., Scott, D. and Dow, M. (1961) Functional Electrotherapy in stimulation of the peroneal nerve synchronized with the swing phase of gait in hemiparetic patients. *Arch Phys Med Rehabil* 42, 202-205].

The development of FES-based Drop Foot correction has gone through the following evolutionary stages:

(i) Hard-wired Single-channel Surface Drop Foot Stimulators,
(ii) hard-wired Multi-channel Surface Drop Foot Stimulators,
(iii) hard-wired Single-channel Implanted Drop Foot Stimulators,
(iv) microprocessor-based Surface and Implanted Drop Foot Stimulators,
(v) alternative sensors as replacement for the Foot-switch: (a) artificial sensors, and (b) "natural" sensors.

(i) Hard-wired Single-channel Surface DFS: As indicated above, the first reported use of electrical stimulation for Hemiplegic Drop Foot Correction was in 1961 by Liberson who proposed to elicit dorsiflexion in a hemiplegic foot, synchronised with the swing phase of gait. Liberson's solution, shown in FIG. 1, comprised power and control box (1), a heel-switch (2), when open, during swing, open-circuits the shunt resistor (3), and enables the delivery of stimulus current across the stimulation electrodes (4). The switch when closed, during stance, connects the shunt resistor across the output of the stimulator and no stimulus is delivered to the stimulation electrodes. The delivery of stimulus to the electrodes positioned for stimulation of the common peroneal nerve) is therefore triggered when the heel-switch opens at reel-off and is terminated when the switch closes at heel-strike. The application of stimulus is thus synchronised with the swing phase of gait. This is an example of a hard-wired stimulator, where the functionality of the stimulator is determined by the wiring of the electronic circuitry. The system performed the essential task of inducing dorsiflexion in the subject's hemiplegic foot at the appropriate point in the gait cycle. Clearly, however, the functionality of the system lacked sophistication and delivered stimuli in a crude fashion compared to the natural performance of the foot-lifter neuromuscular system.

(ii) Hard-wired Multi-channel Surface Drop Foot Stimulators: The first group to present a major technical innovation on Liberson's design was Kralj and his co-workers from the University of Ljubljana in Slovenia. They proposed in 1971 the use of multiple channels of stimulation in the drop foot stimulator and a radio link between the heel-switch and the stimulator [Kralj, A., Trnkoczy, A. and Acimovic, R. (1971) Improvement in Locomotion in Hemiplegic Patients with Multichannel Electrical Stimulation. In: *Anonymous Human Locomotor Engineering—A review of developments in the field including advances in prosthetics and the design of aids and controls*, pp. 45-50. Institute of Mechanical engineers]. The proposed stimulator had three stimulation channels enabling different muscle groups to be controlled independently, such as ankle dorsiflexors and knee flexors and extensors.

(iii) Hard-wired Single-channel Implanted Drop Foot Stimulators: The next major development in hemiplegic drop foot correction technology was the investigation of the possibilities and practicalities of implantable Hemiplegic Drop Foot Stimulators. Jeglic et al., proposed an implanted DFS (IDFS) aimed at overcoming problems of discomfort due to stimulation pain and difficulties experienced by subjects in correctly placing the stimulation electrodes [Jeglic, A., Vanken, E., Benedik, M., "Implantable muscle/nerve stimulator as part of an electronic brace", in *Proc. 3$^{rd}$ International Symposium on External Control of Human Extremities*, 1970, pp. 593-603]. Jeglic et al's single channel stimulation device was never successful but may be seen as pre-dating the development of a commercial, implantable, drop foot stimulator by the Rancho Los Amigos Medical Centre/University of Southern California group in California, in conjunction with Medtronic Inc. of Minneapolis [Waters, R. L., McNeal, D.

and Perry, J. (1975) Experimental Correction of Foot-drop by Electrical Stimulation of the Peroneal Nerve. *J. Bone Joint Surg [A]* 57-A (8): 1047-1054].

The three elements of this system, shown in FIG. 2, are: an external module with a transmitting antenna and control module (10), an implanted assembly comprising a receiver, pulse train generator and bipolar electrode (11) and a heel-switch (12) located in the shoe. In common with the Jeglic et al. system, the implanted device required no batteries as electrical power was supplied by electromagnetic induction. The antenna transmitted a radio-frequency signal through the skin and this was taped to the skin directly over the implant. Two incisions were required: one on the medial aspect of the thigh to implant the receiver, another on the lateral aspect of the leg, below the knee, to expose the common peroneal nerve. The system was never put on the market, presumable due to the relatively extensive surgical procedures required.

(iv) Microprocessor-based Surface and Implanted Drop Foot Stimulators: The first use of micro-controller/microprocessor technology for DFS systems is thought to be the incorporation of microprocessor technology into the previously discussed Multi-channel Surface Stimulators.

A primary motivation for the development of such multi-channel implantable stimulators was to overcome the particular problem with single-channel implanted systems reported by Waters et al. [Waters, R. L., McNeal, D., Faloon, W. and Clifford, B. (1985) Functional Electrical Stimulation of the Peroneal Nerve for Hemiplegia—Long-Term Clinical follow-up. *J. Bone Joint Surg [A]* 67-A (5): 792-793]. Waters et al found that some of the subjects implanted with the Medtronic implanted single-channel DFS system walked with excessive inversion or eversion following surgery. This problem was due to incorrect positioning of the electrodes as the correct placement of the electrode is difficult to determine during surgery. A balanced dorsiflexion response when the subject is prone does not guarantee that the same response will be obtained when the subject is upright, weight-bearing and walking.

A solution to the problem of incorrect electrode placement during surgery, and of the tendency of the electrodes to move post-surgery was proposed by Kelih et al. [Kelih, B., Rozman, J., Stanic, U. and KLjajic, M. (1988) Dual channel implantable stimulator. In: Walling a, W., Boom, H. B. K. and de Vries, J., (Eds.) *Electrophysiological Kinesiology*, pp. 127-130. Elsevier Science Publichers B. V. (Biomedical Division)]. They proposed a dual-channel implantable stimulator enabling control of two-degrees of freedom of foot movement, viz. dorsiflexion and eversion. Thus, post-surgery, when the subject started to walk using the implant, the stimulus level on each channel could be adjusted to obtain balanced dorsiflexion.

(v) Alternative sensors as replacement for the Foot-switch: Since Liberson's development of the first drop foot stimulator until the early 1990s, the sensor used in FES-based Drop Foot Correction system had been the foot-switch, however, it has been proposed by several researchers, that it would be desirable to replace the foot-switch as the gait sensor in DFS systems for the following reasons:

(1) Fundamentally the traditionally foot-switch has been a contact sensor, requiring repetitive contact/non-contact of the wearer's foot with the foot-switch, which has major implications for the reliability of the sensor. With a DFS system, the ultimate application of the system requires that the subject brings the system home and wears it each day. For the wearer to accept this device and to overcome gadget intolerance the reliability of the system must be high and failure of any component of the system over a short period, including the gait sensor, is unacceptable.

(2) The accepted long-term approach to the implementation of FES-based UMN-DF correction systems is the use of implanted systems. For a completely implanted system, the ability to implant the gait sensor is desirable and the foot-switch is unsuitable for implantation.

(3) Finally the information provided to the DFS system by a foot-switch is very limited, namely, presence or absence of contact by a part of the foot with the ground. This type of signal is quite adequate for the hard-wired DFS systems described, but as the sophistication of DFS systems is increased through the use of more complex control algorithms, the limitation of the foot-switch as a gait sensor should become apparent.

For the reasons outlined, several researchers have evaluated alternative gait sensors using either an artificial gait sensor which would be suitable for implantation or using the body's "natural" sensors. Developments in these two research areas will now be discussed.

(a) Artificial sensors as replacement for the Foot-switch: One of the first groups to propose alternatives to the foot-switch as a gait sensor in DFS systems was Symons et al. at the Rancho Los Amigos Medical Centre/USC [J. Symons, D. McNeal, R. L. Waters, and J. Perry, "Trigger switches for implantable gait stimulation," in Proc. 9th Annual RESNA Conference, 1986, pp. 319]. Symons carried out preliminary evaluation of an in-house accelerometer fitted to the greater trochanter process of the femur in a vertical orientation to detect the heel strike event. One of the advantages of accelerometers is that they are miniaturised integrated electronic components and as such are highly reliable and therefore very suitable candidates for implantation, which was the rationale for the evaluation of the accelerometer.

Willemsen et al from the University of Twente in the Netherlands, proposed the used of an integrated accelerometer as a replacement for the foot-switch in an UMN-DF correction system [Willemsen, A. T. M., Bloemnof, F. and Boom, H. B. K. (1990) Automatic Stance-Swing Phase Detection from Accelerometer Data for Peroneal Nerve Stimulation. *IEEE Transactions Biomedical Engineering* 37 (12): 1201-1208]. In their paper, an arrangement of four commercial single-axis accelerometers was placed on the shank of a subject, as shown in FIG. 3. Willemsen et al was able to distinguish between different phases of the gait cycle using the equivalent acceleration at the ankle joint as calculated from four accelerometers placed at locations 30 and 31 and was thus able to detect the onset of swing (push-off) and the termination of swing (heel-strike). Careful attention was paid to the failure rate of detection of push-off and heel-strike. Out of a total of 106 steps, using three hemiplegic subjects, there were errors in only three steps, which is a very good performance.

U.S. Pat. No. 5,814,093 discloses the use of such an artificial sensor arranged corresponding to below the knee of a user. As has been the tradition until now, the (external) stimulation electrodes are placed below the knee joint.

(b) "Natural" sensors as replacement for the Foot-switch: A very elegant and powerful solution to the problems of gait sensors in FES-based UMN-DF correction systems is to use the body's own sensing mechanism. Haugland and Sinkjaer described the use of recordings from a cuff electrode, on the sural nerve, to control the application of stimulus to the common peroneal nerve of a hemiplegic subject [Haugland, M. K. and Sinkjaer, T. (1995) Cutaneous Whole Nerve Recordings Used for Correction for Foot-drop in Hemiplegic Man. *IEEE Transactions Biomedical Engineering* 3 (4):307-317]. The device is shown in FIG. 4, and consisted of a power and control box 40, a set of surface electrodes 41 for stimulation of the peroneal nerve below the knee, a nerve cuff electrode 42 implanted around the sural nerve 43, having percutaneous wires 44 that with a connector 45 could be connected with the power and control box. To reduce noise in the nerve signal recording an external reference electrode 46 was strapped around the leg. The sural nerve is a sensory nerve which has as it sensory input touch sensors on the lateral part of the foot 47. It was proposed that the conventional heel switch in a DFS system be replaced by a single sural nerve cuff which monitored whether or not the affected foot was supporting weight and used this information to control the application of stimulus in the DFS. Recording nerve signals is referred to as Electroneurography and the corresponding signal is called an ElectroNeuroGram (ENG). It was thus demonstrated that nerve recordings could be used as the basis for the control of a DFS eliminating the need for an external foot-switch and its associated problems.

SUMMARY OF THE INVENTION

Having regard to the above discussion of the related prior art, the present invention has as its object to provide concepts, methods and implantable systems which are more user-friendly than the systems hitherto proposed, including the system proposed by the present inventors in 1995 and discussed above. More specifically, it is an object of the invention to provide concepts, methods and implantable systems which significantly
- improves the reliability of the system,
- increases the number of applications,
- reduces the amount of surgery to be performed during implantation and,
- preferably, reduces the complexity of the implant.

In the present invention, one or more of the above objects are firstly achieved by implantation of a stimulation electrode proximal to the knee (preferably a multi-channel electrode), for example on the common peroneal nerve 5-10 cm proximal of the knee. This location provides a number of advantages: more room for the stimulation device, less surgical intervention and better protection of the stimulation leads which do not have to cross the knee joint (as would be the case if the implanted electronics were placed above the knee with the electrodes placed below the knee at the conventional stimulation location), improved cosmetics, and thus patient acceptance, as a corresponding external unit can also be placed above the knee and thus more out of sight. This aspect of the invention is based on the realisation that control of lower leg musculature can be achieved by carefully controlling the stimulation of a combined nerve, i.e. comprising a large number of motor and sensory fibres, located much more proximal than hitherto considered possible.

Secondly, one or more of the above objects are achieved by a concept, method and system in which sensing and stimulation electrodes are arranged (or may be arranged) at a single location, located in such a way that it serves as both a neural (or motor) sensing and neural (or motor) stimulating means. This aspect of the invention is based on the realisation that single peripheral nerves with "useful" combinations of sensing and motor fibres can be located and used purposefully. By the term "single location" is meant that the electrodes are arranged in the vicinity of each other on a single peripheral nerve or a single spinal nerve root of a patient, the single location being accessible through a single incision during surgical implantation.

In a preferred embodiment for the method of the invention, a specific useful location is indicated for use in a HDP Correction System, however, the concept has a much broader approach as any kind of neural signal can be detected (also a natural motor-signal) resulting in the application of a stimulating neural impulse (which can also be applied to a sensing nerve).

A first example of an alternative use of the present invention would be to provide a neural interface to an artificial prosthesis and based, for example on the Median, Radial and/or Ulnar nerves in the arm or the Sciatic nerve (or branches hereof, i.e. Tibial and Peroneal nerves) in the leg. Efferent signals are recorded from one or more nerve stumps in the amputated limb. These signals are then used for controlling the movement of the actions of the prosthesis. By proper transformation of the signals into actions of the prosthesis, control of the prosthesis can become as natural as controlling a normal limb. Further, artificial sensors on the prosthesis can provide relevant feedback information about e.g. force and position, which is then relayed back to the user by stimulating the afferent fibres in the nerve stumps. In this way the user can obtain sensation from the prosthesis that feel as if they came from the amputated limb.

A second example of an alternative use of the present invention would be to provide bladder control in patients with detrusor hyper-reflexia such as spinal cord injured, multiple sclerosis and Parkinson patients based on, for example, Sacral nerve roots. Implantable stimulators exist for controlling voiding in spinal cord injured subjects, however, these systems have no means for detecting when the bladder is full and thus needs emptying. Further, they are incapable of detecting the involuntary, reflex mediated bladder contractions often experienced by the same patients. These involuntary contractions often lead to incontinence and effectively a very small bladder capacity. To avoid this the sensory parts of the nerve roots are often cut as part of the procedure of implanting a void-controlling stimulator. With a combined stimulating and recording electrode it would be possible to detect bladder fullness as well as the reflex contractions from these nerve roots. As it is possible to arrest bladder emptying by stimulation of e.g. the pudendal nerve, the availability of information about the onset of reflex contractions will make it possible to stop them. The method of recording natural nerve activity while at the same time being able to stimulate, might thus make it possible to avoid incontinence without cutting the sensory nerve roots, while at the same time being able to inform the user when the bladder is full.

A third example of an alternative use of the present invention would be applied in a continent stoma. The stoma can be formed by e.g. diverting a muscle from its normal anatomical site and reconfiguring it as a sphincter. Electrical nerve stimulation will be used to make the muscle contract and thus close the stoma aperture. As fatigue is a problem when using striated muscles for production of constant force over prolonged time, it is important to reduce the stimulation to the minimally required. Immediately after emptying the bowel, the stimulation intensity can be low. However, when the pressure in the bowel becomes larger than the pressure produced by the stimulated muscle, the muscle will lengthen and an opening will start to occur that, if nothing is done, will lead to incontinence. As the muscle used as the new sphincter contains muscle spindles, it is possible to record the activity from these by means of the same electrode as is used for activating the motor fibres. The initial lengthening of the muscle can be detected from the spindle activity and be used for making the stimulation intensity increase. In this way the sphincter is kept closed at all times with the minimum muscle force which reduces fatigue. Further, as the stimulation intensity will now monitor the pressure in the bowel, it is possible to provide the system with an alarm, telling the user when it is time to empty the bowel.

A fourth example of an alternative use of the present invention would be to "amplify" a nerve signal to improve a muscle contraction or to improve sensation. A weak nerve signal recorded from a nerve can be used, by proper transformation, for controlling a stimulus to the same nerve, thereby adding to the naturally occurring activity in the nerve. This can either be done by stimulating more nerve fibres than are already active or by stimulating the already active nerve fibres with a higher frequency (or both). In this way a too weak voluntary muscle contraction can be converted into a strong and functional movement. This could e.g. be applied on the peroneal nerve in stroke patients who have a decreased (rather than completely missing) voluntary drive to the foot dorsiflexor muscles or on the soleus or LGS nerves in the same patients to increase the contraction of the ankle plantarflexor muscles to improve the "push-off" phase of walking. Applied on sensory nerves, patients with reduced sensation can have the sensation increased from a part of the body.

A fifth example of an alternative use of the present invention would be to perform controlled decrease of activity in a nerve. A nerve cuff electrode can be used for producing unidirectional antidromic action potentials in a nerve that by collision block stops naturally occurring activity in the nerve. A method to control the level of blocking is to monitor the activity passing the blocking electrode while the same electrode is used for production of the blocking potentials. In this way a closed-loop control algorithm can be provided for regulating the level of stimulation so as to control the natural activity that is allowed to pass by the electrode and continue to the innervated organ or muscle. One practical application of this could be to control the activity in the autonomic nerves innervating the heart (the vagal cardiac branches and the sympathetic cardiac nerves) under (cardio)pathological conditions.

A sixth example of an alternative use of the present invention would be to prevent involuntary spastic skeletal muscle contractions. Efferent signals are recorded from one or more nerves innervating the spastic muscles. When efferent nerve signals are recorded at times when the user wants the muscles to be relaxed, these nerve signals are used to activate a unidirectional antidromic stimulation pattern that by collision block of the nerve action potentials prevents the efferent nerve signals to reach the muscles and thereby prevent or stop a spastic muscle contraction.

According to a first aspect of the present invention, there is provided apparatus for producing a dorsiflexion of the foot of a patient comprising a combined sensing and stimulation electrode device having neurosense and stimulation electrode means capable of sensing a nerve signal from a peripheral nerve and stimulating peripheral motor nerve fibres, wherein said neurosense and stimulation electrode means are implantable above the knee of a patient, means for receiving and processing the sensed nerve signals to identify a signal indicative of the timing of heel strike and heel lift of the patient and for producing a control signal in response thereto, and means for operating said neurosense and stimulation electrode means in response to the control signal to produce stimulation of the peripheral motor nerve fibres.

In a preferred embodiment, the neurosense and stimulation electrode means comprise at least one combined sensing and stimulating electrode configured for arrangement on a single peripheral nerve.

Preferably, the apparatus further comprises means for switching each combined sensing and stimulation electrode between a sensing state and a stimulating state. In an embodiment, the means for switching each combined sensing and stimulating electrode between a sensing state and a stimulating state comprises at least one opto-coupled field effect transistor.

Alternatively and/or additionally, the neurosense and stimulation electrode means comprise at least one neurosense electrode configured for arrangement on a peripheral nerve for sensing a nerve signal from the peripheral nerve, and at least one stimulation electrode configured for arrangement on a peripheral nerve for stimulating a peripheral motor nerve fibre. In a preferred embodiment, the at least one neurosense electrode and the at least one stimulation electrode are configured for arrangement on the same peripheral nerve.

In an alternative embodiment, the at least one neurosense electrode and the at least one stimulation electrode are configured for arrangement on adjacent peripheral nerves and are arranged to be located just next to each other.

Preferably, the apparatus further comprises implantable communication means for enabling communication between the operating means and a computer located external to a patient's body, said communication means being arranged to receive and/or store programs for use by the operating means.

In a preferred embodiment, the receiving and processing means comprise first and second receiving and processing means, wherein the first receiving and processing means are arranged to process a signal received from the neurosense and stimulation electrode means and to provide a first serially coded signal for transmitting to said second receiving and processing means, the second receiving and processing means comprise means for receiving the first serially coded signal, identifying the signal indicative of the timing of heel strike and heel lift, providing a second serially coded control signal in response thereto and transmitting the second) serially coded control signal to the operating means, and the operating means are configured to decode the second serially coded control signal and to provide a control signal for transmission to the neurosense and stimulation electrode means.

Preferably, the first receiving and processing means and the operating means are housed in the same device. More preferably, the device housing the first receiving and processing means and the operating means is implantable above the knee of a patient. More preferably, the device housing the first receiving and processing means and the operating means is implantable in the thigh of a patient.

In an embodiment, the apparatus further comprises a power source for powering the first receiving and processing means and the operating means, wherein the power source is a rechargeable battery located in the device housing the receiving and processing means and the operating means. Preferably, the rechargeable battery is inductively chargeable by a second power source located external to a patient's body.

Alternatively and/or additionally, the apparatus further comprises a power source for powering the first receiving and processing means and the operating means, wherein the power source is located external to a patient's body. The apparatus may further comprise a power source for powering the operating means, wherein the power source is implantable with the operating means.

In a preferred embodiment, signals between the first receiving and processing means and the second receiving and processing means are transmitted cordlessly through a patient's skin.

In a preferred embodiment, one or more of said sensing, stimulating and combined sensing and stimulating electrodes are located in a single cuff and the cuff is configured for arrangement around a single peripheral nerve. Preferably, the peripheral nerve is the common peroneal nerve. Alternatively, the peripheral nerve may be the sciatic nerve.

In an alternative embodiment, one or more of said sensing electrodes are located in a first cuff and the first cuff is configured for arrangement around a first single peripheral nerve and one or more of said stimulating electrodes are located in a second cuff and the second cuff is configured for arrangement around a second single peripheral nerve adjacent the first peripheral nerve.

Preferably, the first peripheral nerve is the tibial nerve and the second peripheral nerve is the common peroneal nerve.

In a preferred embodiment, said neurosense and stimulation electrode means are implanted above the knee of a patient. In an alternative embodiment, said neurosense and stimulation electrode means, first receiving and processing means and operating means are implanted above the knee of a patient.

In an alternative, embodiment, said neurosense and stimulation electrode means are implanted above the knee of a patient and said first receiving and processing means and operating means are implanted in the thigh of a patient.

It is to be noticed that the at least one neurosense electrode means and the at least one stimulation electrode means are not necessarily provided as separate electrodes by may be incorporated in a combined electrode, further means being provided for switching each such combined between a neurosense electrode state and a stimulation electrode state. In this way the most "compact" implementation of an apparatus according to the invention would comprise a single combined electrode in combination with corresponding switching means.

As will be apparent from the above disclosure of the prior art, it is often desirable to provide a plurality of electrodes in a multichannel set-up, this providing enhanced control of both the sensing and stimulation aspects of the given implementation. However, the more channels the more conductors will have to be used to transmit signals between the electrodes and the processing means, this adding to the bulk of the implanted device as well as to the fragility. Accordingly, in a preferred embodiment of the invention, means are provided allowing a reduced number of conductors to be used as compared to the number of electrodes, preferably by transmitting the signals serially coded and providing the corresponding means for coding and de-coding the signals.

BRIEF DESCRIPTION OF THE DRAWINGS

Embodiments of the invention will hereinafter be described, with reference to the accompanying drawings, in which.

DETAILED DESCRIPTION OF PREFERRED EMBODIMENTS OF THE INVENTION

A first embodiment in accordance with a first aspect of the invention will be described with reference to FIG. 5-7. As can be seen from FIG. 5, the system comprises an implantable multichannel stimulator with a multipolar nerve stimulation electrode implantable on the peroneal nerve. Further it has an external unit, that powers and controls the implant based on an external switch placed under the heel of the user. During gait, the heel-switch makes the stimulation turn an during the swing phase of the affected leg and off during the stance phase, to make the dorsiflexor muscles actively lift the foot clear of the ground during swing and to relax the dorsiflexor muscles during stance.

Peroneal Nerve (Implant Site for Stimulation Electrode)

Figure 6:
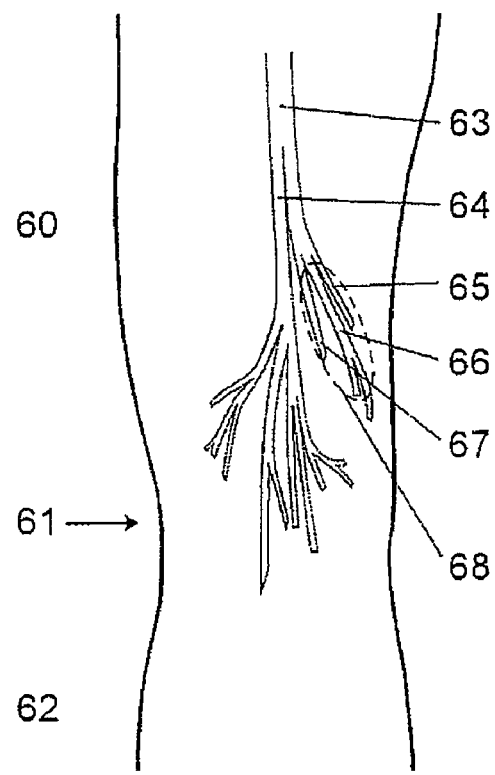
FIG. 6 shows a posterior view of the right popliteal fossa, the location for stimulation electrode on common peroneal nerve being indicated by a ring.
Figure 7:
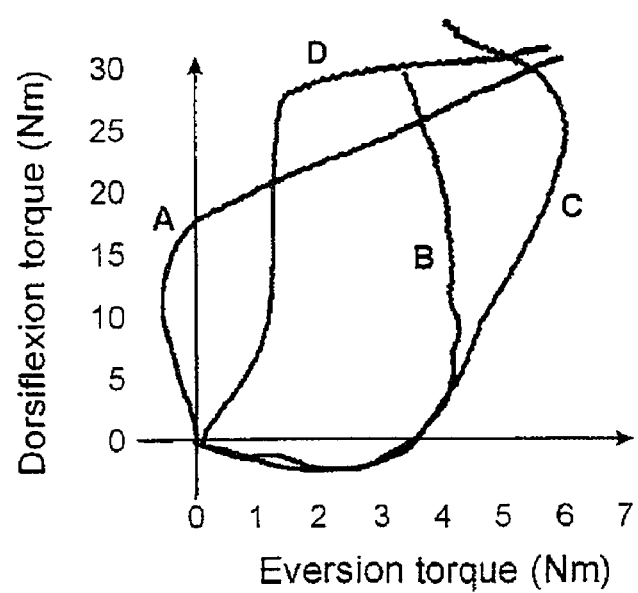
FIG. 7 shows an example of torques measured around the ankle joint from a human subject, when stimulating the different sets of electrodes in a 12-polar nerve cuff electrode implanted on the common peroneal nerve proximal to the knee.

In FIG. 6 is shown a schematic posterior view of the popliteal fossa in the right leg, showing the thigh 60, knee 61, calf 62, Sciatic nerve 63, Tibial nerve 64, cutaneous branch of the Common Peroneal nerve 65, the Common Peroneal nerve 66, the Sural Communicating nerve 67 and the preferred location for the stimulation electrode 68. The stimulation electrode is preferably implanted around the common peroneal nerve (CP), 5-10 cm proximal to the knee, excluding the cutaneous nerves that branch off the CP at this level. In this location the electrode is protected by the two groups of tendons bordering the popliteal space. Further, while it includes only few cutaneous fibres, it includes nerve fibres to practically all the muscles that dorsiflex the foot, i.e. muscles which: invert and dorsiflex the foot (tibialis anterior and extensor hallucis longus); dorsiflex and invert the foot (extensor digitorum longus and peroneus tertius); and evert and plantarflex the foot (peroneus longus)

This location of the electrode further has the advantage over locations below the knee, (which have hitherto been used) that the lead-wires can be passed to a suitable location for the main body of the implant, e.g. in the upper thigh or in the abdomen, without having to cross the knee joint. Hereby the risk of lead breakage is reduced.

The stimulation electrode can be of many different designs. The common feature is that it should have several electrical contacts placed either inside or in the immediate vicinity of the nerve to be stimulated. The contacts should be placed so that when passing an electrical current through them, different parts of the nerve will be activated. In a preferred embodiment, the electrode is an insulating structure that comprises a number of electrode contacts that provide an electrical interface to the nerve. The contacts should be placed so that when passing an electrical current through them, different parts of the nerve will be activated.

The electrode means consists of one or more electrodes and a mechanical device supporting their fixation onto the nerve. In a preferred embodiment, a nerve cuff electrode, which in principle is a tube of an insulating material (such as silicone) with a number (possibly 12) of metal contacts (such as platinum, platinum-iridium or stainless steel) located within the cuff wall. The tube is opened in one side to make it possible to install around the nerve, and a locking mechanism is used to close the cuff hereafter.

In a preferred embodiment a silicone cuff with 12 platinum electrode contacts, arranged as four tri-poles inside the cuff, is used. Each tri-pole having the outer contacts short-circuited with a wire located inside the cuff wall, resulting in only eight wires exiting the cuff. The cuff is in a preferred embodiment ca. 20 mm long and has an inner diameter approximately 20% larger than the nerve (typically 5.2 mm). In tests, this type of electrode has shown to provide enough selectivity in the stimulation to have adequate control of foot movement for the purpose of rehabilitation of foot drop.

In a first embodiment a multichannel stimulator is located in a separate housing and connected to the stimulation electrode by means of a multi-lead cable. The cable has an in-line connector that can be assembled during surgery, to facilitate the passing of leads under the skin. The stimulator may have the following approximate dimensions: thickness=6 mm, length=60 mm, width=30 mm. In a preferred embodiment, the stimulator is implanted in the upper thigh of a patient. Thus, an external component of the device that communicates with the stimulator can be strapped to the upper thigh of the patient or held in a pocket of an item of clothing worn by the patient. The purpose of the stimulator is to deliver electrical pulses to the contacts in the stimulation electrode. Usually these pulses will be charge-balanced and current-controlled pulses, such as to minimise electrochemical processes at the electrode site and hereby reducing the risk of damage of electrodes and surrounding tissue. The stimulator is powered and controlled via an inductive link across the skin. The stimulator can be implemented in various ways. The stimulator may be analog, having separate channels that are each powered and controlled with a separate inductive link, running at its own frequency (in a two channel system this could be 1.1 MHz and 4.4 MHz resp.). The device has been implanted in a small number of patients and has been used on a daily basis by these patients. This stimulator produces fixed-current, biphasic pulses that are pulse width modulated by the external transmitter.

Another implementation of the stimulator could be by means of digital electronics. This method would be much to prefer, as it makes it possible to establish a serial communication channel via the inductive link and in this way program many more parameters of the stimulation. Furthermore, only a single inductive link will be necessary to support any number of channels. A problem remains with the implant system as described above. Each contact in the electrode requires a separate conductor in the cable (unless some contacts are connected directly in the electrode). If it is wished to use many channels of stimulation, then the cable between stimulator and electrode becomes very thick, which is very impractical and more prone to be damaged by movement as well as increasing the risk of damage to the nerve on which the electrode is placed.

A solution to this is to place a part of the stimulator directly on the electrode. It could then be made so that the cable only has to carry power and serially coded information from the main body to the electrode. At the electrode, this information is then decoded and stimulation pulses distributed to one or more of the contacts. In this way the number of conductors in the cable can be reduced to somewhere between two and four. This solution requires the electrode-part of the circuit to be extremely miniaturised; otherwise it will not fit on the electrode. A way to do this is by implementing it as a custom made integrated circuit. The above aspect of serially coding information also applies to embodiments in which a plurality of channels is used for both sensing and stimulating as will be described below. In such an embodiment the implanted electrode-part should compromise means for serially coding the sensed signals, for subsequent transmission to the processing means, and corresponding means for de-coding serially coded signals transmitted from the stimulator.

On the surface of the skin over an implanted portion of the device, coil(s) for transmitting power and control information to the implant may be placed. The coils are connected to a device with batteries, control circuitry and a power amplifier for powering the inductive link.

This unit can be designed in various ways. In a specific embodiment it has been implemented with a micro-controller, that stores a program for communicating with the implant and that stores the parameters for the stimulation. The unit has inputs for power from a battery, signal from a heel-switch and a serial input channel for programming stimulation parameters into the unit. It further has a connector for downloading a new program into the unit.

In an alternative embodiment, power is supplied to the stimulator by a chargeable battery located in the implanted stimulator. The rechargeable battery may, for example, be a lithium-ion battery that may be inductively charged by an external charger.

A radio receiver is optional, but facilitates the programming of parameters into the device from the programming unit and makes it possible to have a wireless heel switch, as will be described below. A receiver built by the present inventors has been based on one of the miniature transceiver circuits that are available commercially now (e.g. from RF Monolithics, Inc.). It provides a digital signal to the serial input on the power and stimulus control unit and simply replaces a standard RS-232 cable.

In order to set up the system for a specific patient, a programming unit is necessary. This can be either a handheld dedicated unit, or a PC with a suitable program. If the power and stimulus control unit is equipped with a radio receiver, the programming unit should have a corresponding transmitter, to make it possible to transfer stimulus parameters without wires to the power and stimulus control unit.

This programming unit makes it possible to set the following parameters for the stimulation:
  threshold and maximum stimulation for each channel
  stimulation frequency for each channel
  the time allowed for ramping up the stimulation when the heel is lifted from the ground for each channel Including a ramped on/off is important for many of the patients, as simply turning on and off the stimulation abruptly will often cause a stretch reflex to be initiated in the ankle plantar- and dorsiflexor-muscles respectively. The reflex is caused by too fast movement of the joint and will always work against the desired movement. Choosing a suitable ramp speed for each of the activated channels can eliminate this reflex.

In a present embodiment the stimulation intensity is kept constant during the swing phase of the leg (after ramping up to the specified level), however, in future embodiments it may prove beneficial to vary the intensity during the swing phase as well as for a brief period after foot-to-floor contact. Potential fatigue and discomfort of the stimulation may be reduced if the stimulation intensity is decreased during part of the swing phase. Further, it may be beneficial to increase the stimulation intensity for a brief period after the heel contacts the floor, to counteract the mechanical effects of the reaction force from the floor acting upwards on the heel, which can cause the front part of the foot to come down faster than preferred by the user.

Apart from the "advanced" programming unit, the patient nay be provided with a box, that in a simple way (e.g. with a turnable knob or slider) can set the stimulation intensity and/or the balance between inversion and eversion, within a limited range set by the therapist. This user interface may well set many or all of the stimulation parameters, but the user should have only one or two knobs to set. An intelligent routine in the programming unit then sets the specific parameters based on the users command.

Heel Switch with/without Radio Transmitter

In the first preferred embodiment, the stimulation is controlled by a sensor placed in the shoe of the user. This sensor can be a standard heel switch connected to the power and stimulus control unit with a cable, or it can be different kind of sensor giving information about foot-to-floor contact. Further, the cable can be replaced with a wireless communication link.

In this first preferred embodiment the switch means has been implemented as a wearable garment that is mounted on the ankle of the user. An ultra-thin sensor (in this case a force sensitive resistor from Interlink Electronics, Inc.) is sewn into the garment at a location under the heel. This sensor could also be made from a piezoelectric film, which has the advantage that it can provide power to parts or all of the electronic circuit in the device. On the garment above the ankle is placed a compact unit containing a battery, a transmitter (from RF Monolithics, Inc.) and a standard microcontroller. The microcontroller is usually in a "sleep mode", where it consumes only very little energy. When the user either steps on the sensor or releases the weight from it, the controller wakes up, transmits an identification number (to avoid interference with other similar systems in the surroundings) and then one of two possible codes (one for heel strike and one for heel lift) to the power and stimulus control unit, and then goes back to sleep. The combination of a wearable garment with the device sewn in, the wireless communication with the power and control box, and the fact that the sensor is very thin, makes it possible for the user to wear it all day even when changing clothes and footwear, to chose practically any type of footwear and even walk without shoes.

Example 1

Three hemiplegic patients were equipped with the first embodiment of the invention. It was tested if the system was able to produce dorsiflexion and if the multi-channel stimulation electrode placed on the peroneal nerve above the knee was able to provide good selectivity so as to control the different movements of the foot. With proper balancing of the different channels of stimulation, it was possible to produce a movement of the foot that was almost pure dorsiflexion, which is the natural movement and thus most cosmetically acceptable and least damaging to the ankle during gait. In FIG. 7 an example of the torques measured around the ankle joint of a human subject with a 12-polar nerve cuff electrode implanted on the common peroneal nerve proximal to the knee. The foot was fixed during the measurements and the isometric torques generated around the ankle were recorded while the stimulation intensity was increased from zero to maximum (pulse width 0-250 μs, current 1 mA, frequency 20 Hz) over a period of 5 seconds. It can be seen in FIG. 7 that the effect of the stimulation on the different channels were quite different, showing a good selectivity of the cuff electrode and showing that the nerve fibres were functionally organised in the nerve bundle. Channel A for low stimulation levels produced a combination of dorsiflexion with inversion, which at high stimulation levels changed to eversion. Channel B produced a combination of dorsiflexion and eversion. Channel C and D produced for low levels a combination of eversion and plantar flexion, which for higher levels changed to dorsiflexion. During gait, relatively low torques are necessary to produce movement, and by selecting a combination of intensities on the different channels, it was possible to produce a natural dorsiflexion of the foot that felt comfortable for the patients (in the presented case by combining channel 1 and 2).

A second embodiment in accordance with the first aspect of the invention will now be described with reference to FIG. 8. Compared to the system shown in FIG. 5, in this system the heel switch has been replaced with a system for using the natural sensory nerve activity recorded from a peripheral nerve going to the foot. As many of the parts for the second embodiment are the same as for the first embodiment, only the parts in FIG. 8 that are different from them in FIG. 5 will be described in the following.

Sensory Nerve from the Foot

Neural information about foot-to-floor contact can be found in several of the nerves innervating the skin of the foot. It may be expected that the best source of such signals will be the nerves innervating the plantar surface. However, the present inventors have found that also nerves innervating other areas of the foot provide enough information about this that it can be extracted and used for control of the stimulator.

Signals from the calcaneal branch of the tibial nerve (innervating the skin on the heel) have been recorded, by implanting a nerve cuff electrode on it, just proximal to the ankle joint [Upshaw and Sinkjaer (1998) Digital signal processing algorithms for the detection of afferent nerve activity recorded from cuff electrodes, *IEEE Trans. Rehabilitation Engineering*, vol. 6, no. 2, 172-181]. This gives a good signal, but the surgical access to the nerve is too difficult for this nerve to be a good candidate for a commercial system.

The sural nerve is a better candidate, as the surgical access to it is much easier. It also gives a signal that is as good as that recorded from the calcaneal nerve. Both signals clearly modulate with the gait cycle and it is possible to detect heel strike and in most cases also heel lift from these signals. The sural nerve can easily be accessed a few centimeters proximal to the lateral malleol, where it is located immediately under the skin.

For surgical reasons it is even better if the signals can be recorded much more proximal, preferably proximal to the knee. This may be possible, as a branch of the common peroneal nerve communicates with the sural nerve (sural communicating branch (67)). This branch can be found just next to where the stimulation electrode is implanted which means that the recording electrode can be implanted through the same surgical incision.

Nerve Recording Electrode

The nerve-recording electrode can be designed in various ways. The common feature is that it will have one or more electrical contacts placed in or around the nerve, so that the naturally occurring activity herein can be recorded, either as a sum of the activity from all the nerve fibres, a sum of the activity from a portion of the nerve fibres or the activity from a single nerve fibre.

In a preferred embodiment a nerve cuff electrode has been chosen, which in principle is a tube of an insulating material (such as silicone) with a number of metal contacts placed on the inside of the tube. The tube, is opened in one side to make it possible to install around the nerve, and a locking mechanism is used to close the cuff hereafter. Our nerve cuff has three internal circumferential electrodes (made of platinum or stainless steel) placed symmetrically in the cuff the at the centre and one at either end). It also has an external electrode, placed on the outside of the cuff, which is used as a reference. The method for recording nerve activity with such electrode has been described in the literature. It provides a signal that is a weighted sum of the activity in all the nerve fibres inside the cuff and gives good rejection of noise signals external to the cuff. It has been shown to give stable signals over long periods of time in chronic implants both in animals and humans.

Implanted Amplifier and Telemeter

The purpose of this unit is to amplify the nerve signal recorded with the recording electrode and transmit it through the skin to the external nerve signal receiver. It can be implemented in various ways, depending on the type of recording electrode. It should amplify the signal from the recording electrode with a suitable amount and optionally do some signal conditioning (such as band-pass filtering, rectification and/or integration) before transmitting the signal through the skin.

In a specific embodiment this has been implemented with a standard instrumentation amplifier, that amplifies the signal with approximately 120 dB and transmits the signal via an inductive link by frequency modulation of the carrier signal. It has a bandwidth of 10 KHz. It is powered via a separate inductive link from the external power transmitter and signal receiver. The two inductive links transmit signals through the same space and are uncoupled by a technique known as morphognostic coils. Briefly this technique is based on shaping the coils so that the summed magnetic flux from one inductive link going through the coils of the other is zero. This is done by making the coils of the power link be shaped as a square and the coils of the signal link shaped as a figure eight. Further the two links run at separate frequencies.

Power Transmitter and Signal Receiver

This unit forms the external part for the implanted amplifier and telemeter. It provides an oscillating magnetic field from which the implant gets its power and it receives the magnetic field from the implant, that carries the amplified nerve signal. This latter magnetic field is picked up by a coil that matches the implanted transmitter coil, and the resulting electrical signal is demodulated to extract the nerve signal.

Signal Analysis

The purpose of the signal analysis unit is to transfer the recorded nerve signal into a signal that replicates that of a heel switch if such had been placed in the shoe of the user. This can be implemented in various ways. The most successful one to date is the following.

Pre-processing: The nerve signal is band-pass filtered to remove artefacts originating from ElectroMyoGraphic signals (EMG) from nearby muscles and to reduce the content of electrode and amplifier noise. The filter cut-off frequencies are chosen based on an optimisation of the signal to noise ratio using signals with known contents of signal and noise. The signal is then rectified and integrated. To remove the artefacts coming from the stimulation pulses, the integration is done in sections between the stimulation pulses, in such way that the integrated sections exclude the periods within which the stimulation artefacts occur. This is a known technique called binintegration. The resulting signal has a much lower bandwidth than the original nerve signal and represents the average amplitude of the nerve signal between each stimulation pulse. This processing can be done either with analog or digital circuitry. In any case the signal must come out of the pre-processing in a digitised format.

Detection of foot-to-floor contact: The digitised pre-processed nerve signal is fed into an adaptive logic network (ALN, available from Dendronic Decisions, Ltd.), which is a type of artificial neural network. This type of network is described in the literature, and consists of a number of so-called linear threshold units and a number of logic nodes. Due to the logic nature of the network it is very simple to implement in a portable device, such as the micro-controller described above. The network takes as input a number of parameters derived from the pre-processed nerve signal and produces as an output a signal that can be used to turn on and off the stimulator. The network is trained by a supervised learning technique, that requires a sequence of data to be recorded from the patient during gait. During this sequence the patient is equipped with sensors under the foot. A set of data with corresponding nerve signal and sensor-signal is presented to the ALN, and the training algorithm optimises the network so that based on the nerve signal it produces an output signal that matches the recorded sensor signal. Once this is done, the artificial sensors under the foot can be taken off and the ALN will control the stimulator based on the nerve signal alone.

Figure 1:
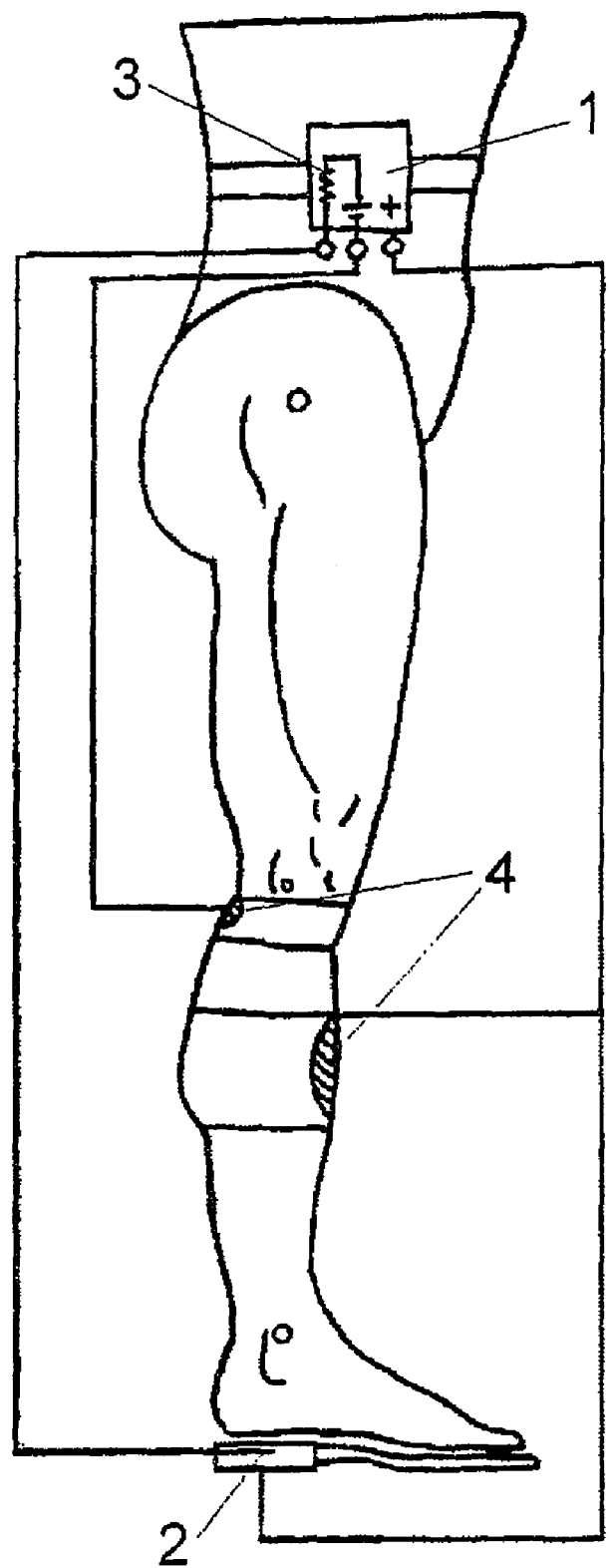
FIG. 1 shows schematically Liberson's solution for a hard-wired Single-channel Surface DFS.
Figure 2:
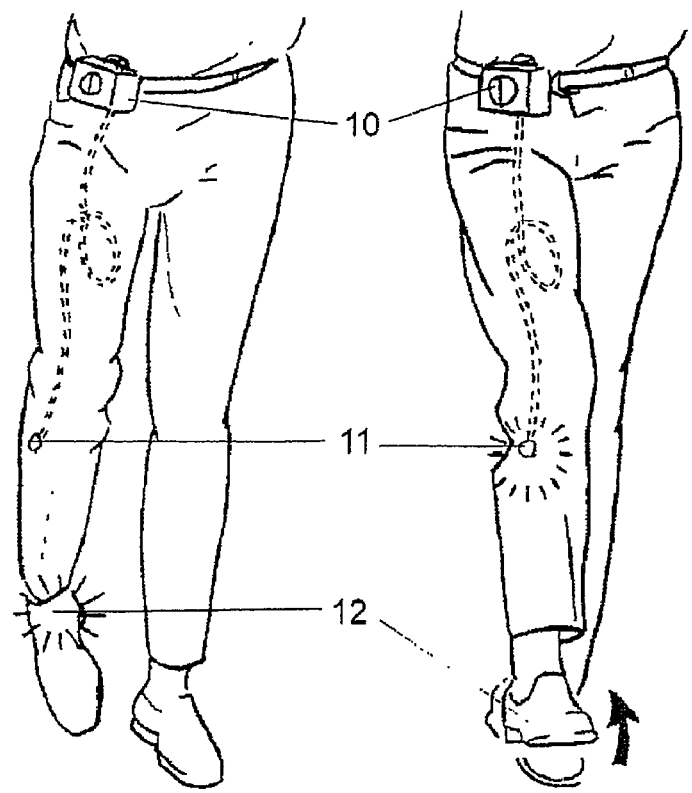
FIG. 2 shows schematically the Rancho Los Amigos Medical Centre hard-wired Single-channel Implanted Drop Foot Stimulator.
Figure 3:
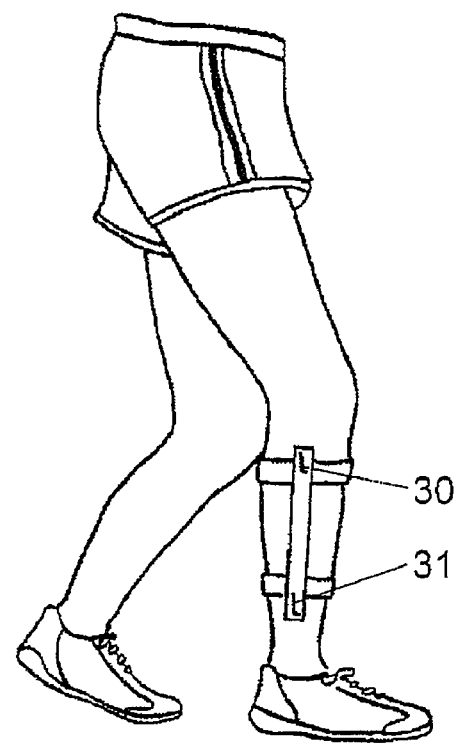
FIG. 3 shows schematically Willemsen's set-up for an artificial sensor as replacement for the Foot-switch.
Figure 4:
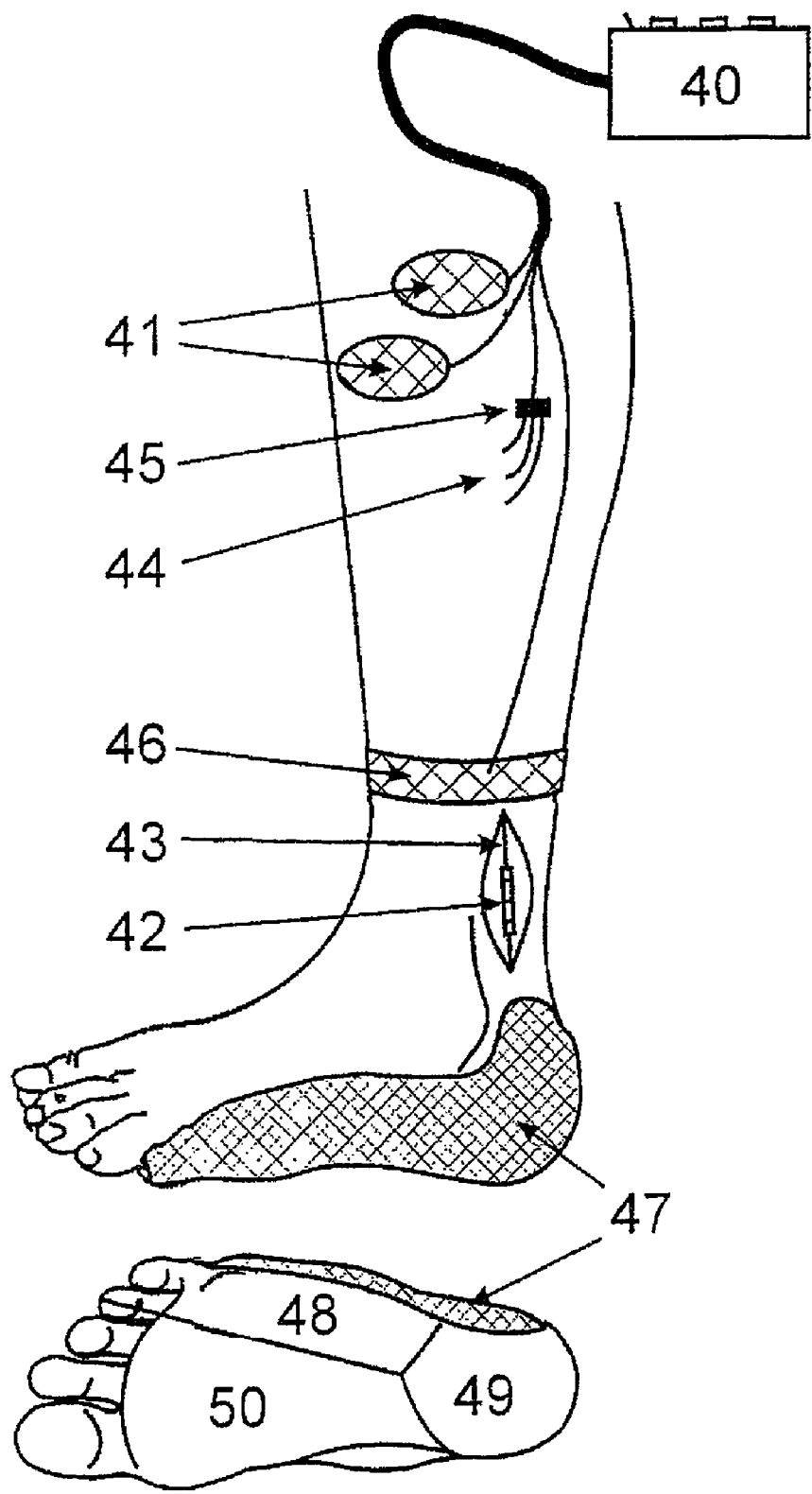
FIG. 4 shows schematically Haugland and Sinkjaers set-up for a natural sensor as replacement for the Foot-switch.

If recordings are made from more than one nerve (e.g. the tibial and the sural or sural communicating branch), it will be possible to detect information about how the foot lands on the floor, e.g. if it lands on the lateral or medial aspect of the foot sole, as different branches of the Tibial nerve innervate other areas of the foot-sole (lateral branch 48, calcaneal branch 49 and medial branch 50, see FIG. 4) compared to the sural nerve 47. This information can then be used for automatic regulation of the relative stimulation intensities to correct for excessive inversion or eversion of the foot. Similarly, if it is detected that the foot lands with the frontal part first, then stimulation intensities can be increased so that better dorsiflexion is obtained to make to foot land with the heel first.

Figure 9:
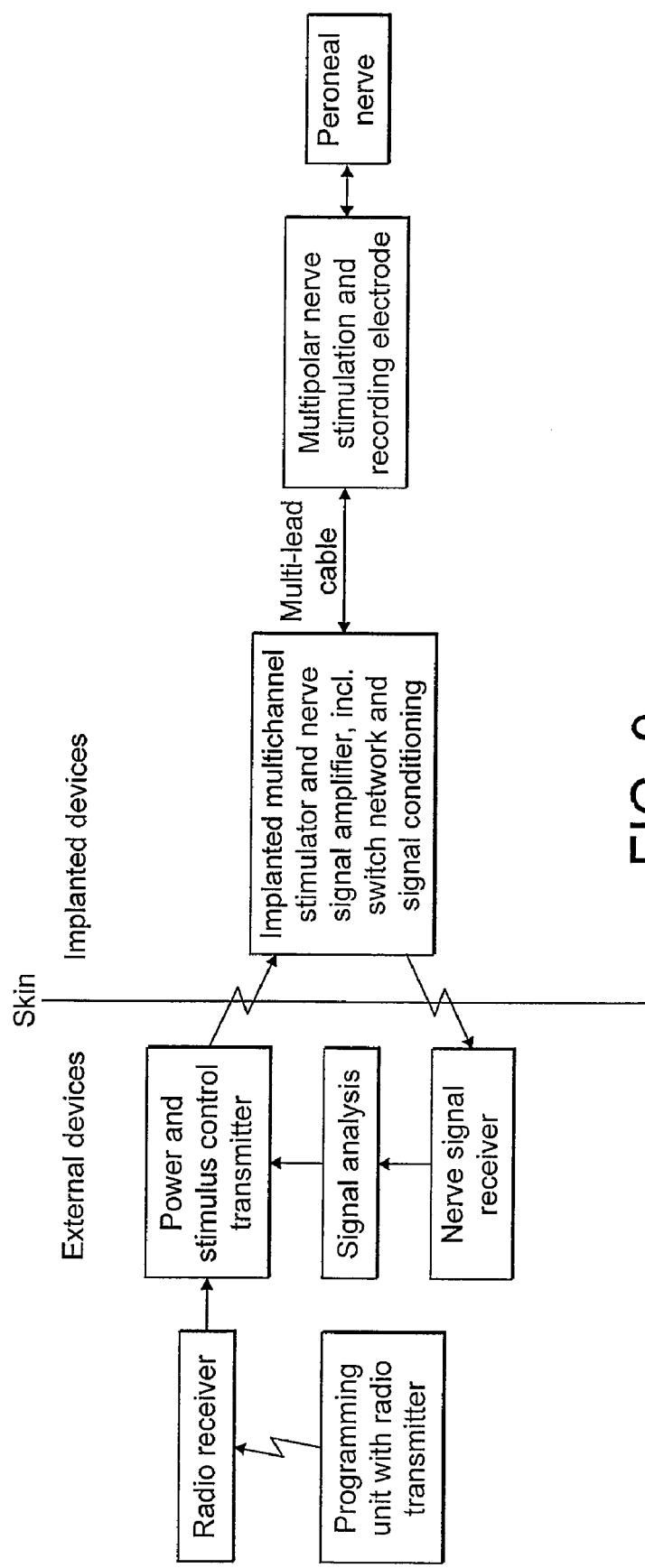
FIG. 9 shows a diagram of drop foot system with combined stimulation and recording electrode implanted on the peroneal nerve.

A third embodiment in accordance with a second aspect of the invention will now be described with reference to FIG. 9. This system combines the stimulation and recording electrode in one. This significantly reduces the amount of surgery to be performed and reduces the complexity of the implant. This can be done because the peroneal nerve contains cutaneous (sensory) fibres going to the foot, and it has proven possible to record information from these sensors with the nerve cuff stimulation electrode described above. The recorded signal modulates clearly with the gait cycle and can be translated into a stimulator control signal in the same way as described in the second preferred embodiment.

Figure 5:
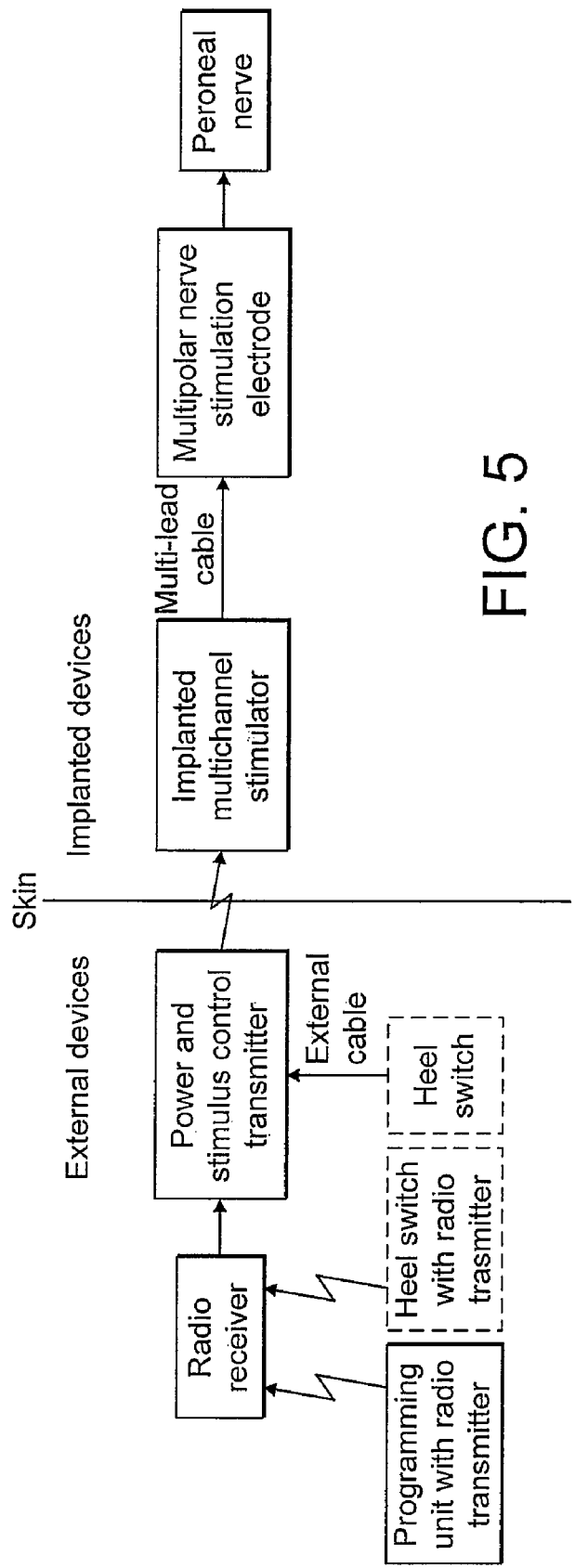
FIG. 5 shows a diagram of drop foot system with implantable nerve stimulator.
Figure 8:
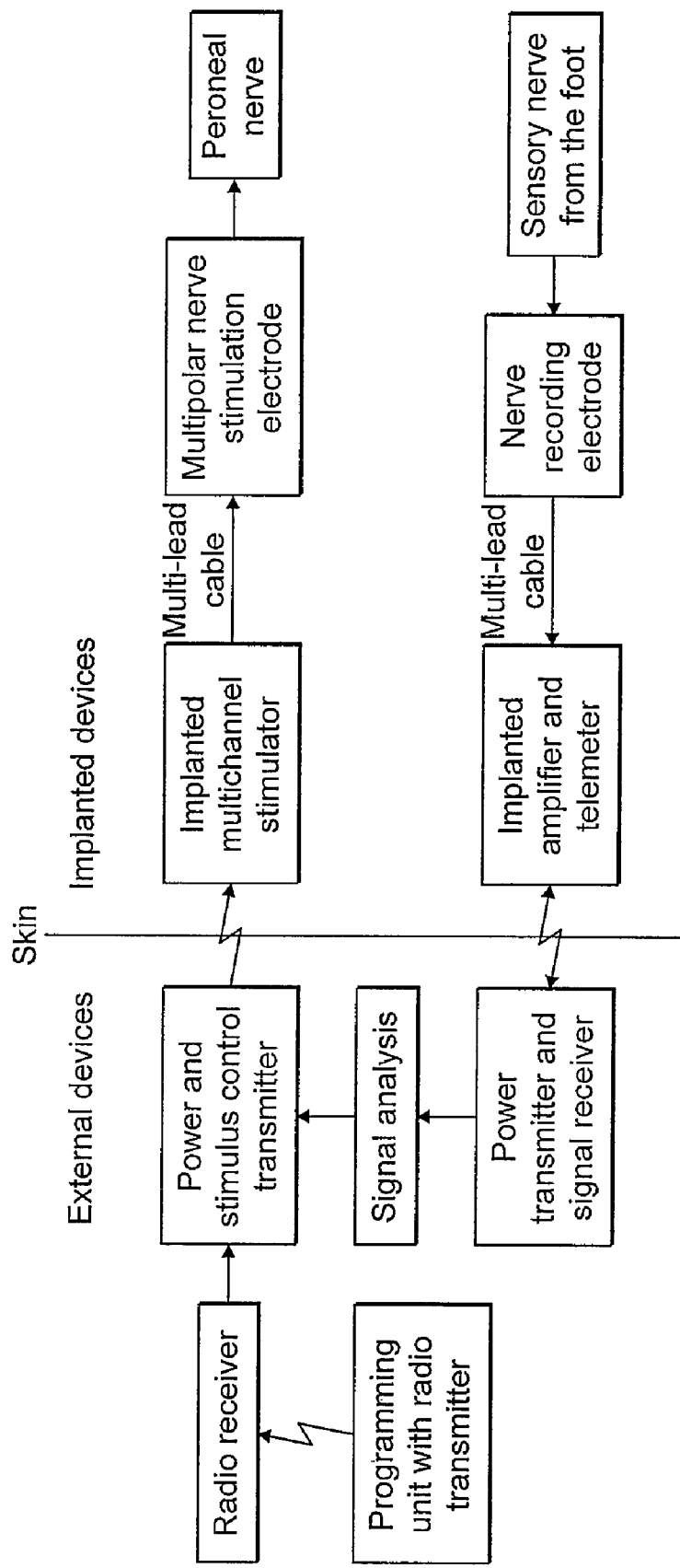
FIG. 8 shows a diagram for a drop foot system with implanted nerve stimulator and nerve signal amplifier for natural sensory feedback.

Compared to the systems shown in FIGS. 5 and 8, most of this third system is the same, except the sensory electrode and its cable are missing and the amplifier and stimulator are built into the same device. This further results in the external equipment being simplified, as only one power transmitter is necessary.

Multipolar Nerve Stimulation and Recording Electrode

This electrode can be designed in various ways. However, the design must fulfil the requirements for both recording and stimulation electrodes. The multipolar nerve cuff as described in the second embodiment is suitable for this.

Implanted Multichannel Stimulator and Nerve Signal Amplifier

This unit can be implemented in various ways. In principle it is only a combination of the stimulator and amplifier described with reference to the first and second embodiments. However, it is necessary with a switch arrangement that can switch the electrode between being connected to either the stimulator or the amplifier.

Preferably, this unit should contain the pre-processing as described with respect to the second embodiment above, as this greatly reduces the necessary bandwidth for the implanted transmitter. If the stimulator is implemented with digital electronics, it can be made able to store information about the parameters of the pre-processing, to that this can be adapted to the specific conditions of the particular patient, nerve, electrode etc. Also, it is then possible to send out the signal in a digital form, and thereby reduce the effect of loss of signal quality in the transmission through the skin.

With the stimulator and the amplifier in this way connected, it is also possible to send other information from the implant to the external unit via the same inductive link as transfers the amplitude of the nerve signal. This information could be e.g. impedance measurements of the electrodes (to test the integrity of these), information about the humidity within the encapsulation (to warn about potential malfunction of the device), information about the coupling coefficient between the external and implanted coils (to facilitate placement of the external unit), information about communication errors (handshaking) etc.

If selective recordings from the different sets of electrodes in the electrode assembly are made, then it will be possible to detect information about how the foot lands on the floor, e.g. if it lands on the lateral or medial aspect of the foot sole. This information can then be used for automatic regulation of the relative stimulation intensities to correct for excessive inversion or eversion of the foot. Similarly, if it is detected that the foot lands with the frontal part first, then stimulation intensities can be increased so that better dorsiflexion is obtained to make to foot land with the heel first.

Example 2

As will be described in the following, the present inventors have demonstrated that a cutaneous nerve signal from the foot can be recorded from the peroneal nerve proximal to the knee, using the same electrode as was used for stimulation of the nerve to dorsiflex the foot. It was also demonstrated that it is possible to record this signal concurrently while stimulating through the same cuff.

Methods

As part of the procedure for testing the implantable foot drop stimulator developed by the present inventors, three hemiplegic patients were instrumented with a 12-polar nerve cuff electrode (20 mm long, 5.2 mm ID) on the common peroneal nerve a few centimeters proximal to the knee. The eight lead-wires to the electrode were for an initial 8-week period taken out through the skin. This procedure allowed direct electrical access to the cuff in this initial period.

Figure 10:
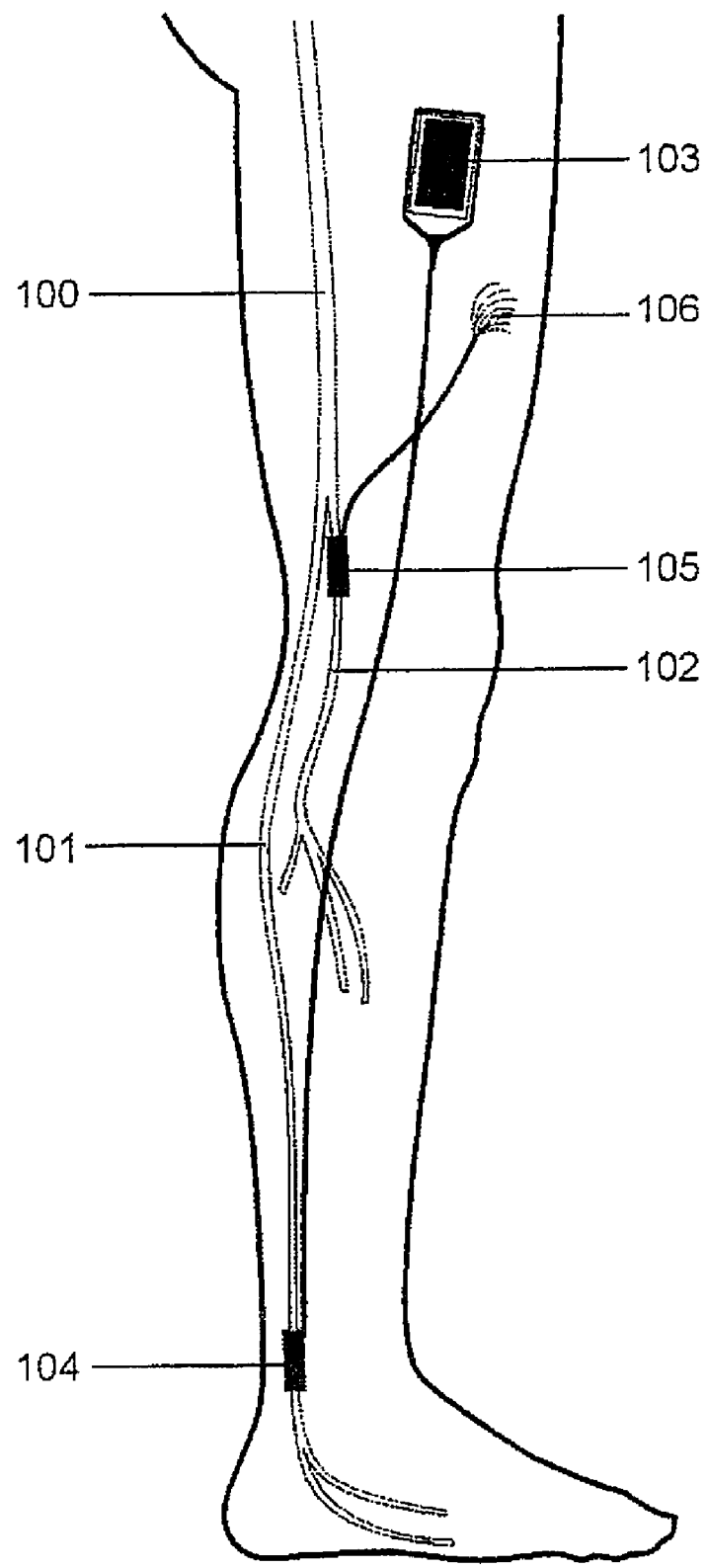
FIG. 10 shows a nerve cuff placed on the sural nerve proximal to the ankle and an implantable amplifier placed subcutaneously at the middle of the thigh.

One of the patients (female, 32 year old) further had a nerve cuff placed on the sural nerve proximal to the ankle and an implantable amplifier placed subcutaneously at the middle of the thigh, see FIG. 10, which shows the Sciatic nerve 100, the Sural nerve 101, the Peroneal nerve 102, the implanted amplifier 103 for amplification of the Sural nerve signal, the Sural nerve cuff electrode 104, the Peroneal nerve cuff electrode 105 and the percutaneous wires 106 from the Peroneal nerve cuff electrode.

Figure 11:
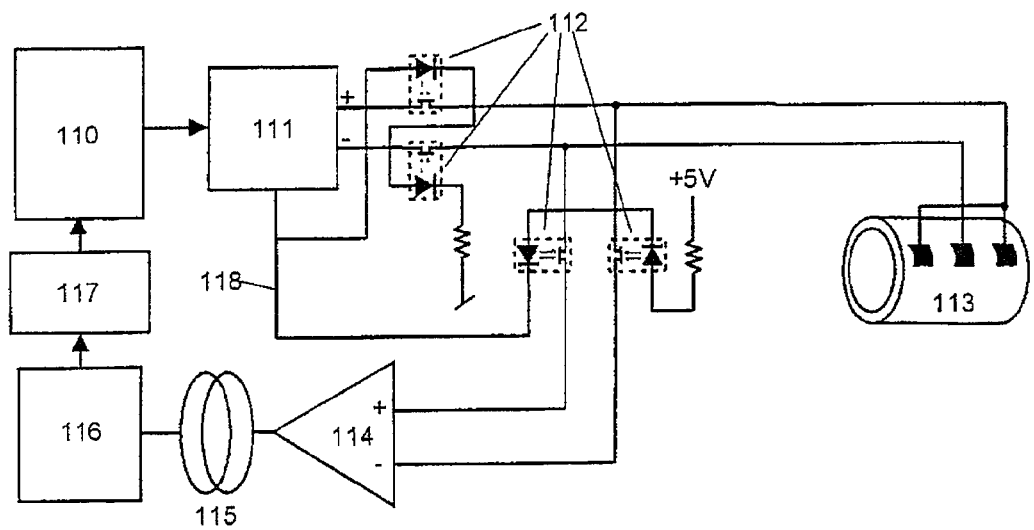
FIG. 11 shows a diagram of a circuit making it possible to record and stimulate through the same cuff electrode.

To make it possible to record and stimulate through the same cuff electrode, an electronic circuit was built, see FIG. 11, consisting of a personal computer 110, a stimulator 111, opto-coupled field effect transistors 112, the electrode 113, an amplifier 114 that transmitted the amplified signal over a telemetric link 115 to a corresponding receiver 116, a bandpass filter 117 filtering the signal to be between 600 Hz to 2500 Hz. Controlled by an output from the stimulator 118, the circuit switched the electrodes to the stimulator while a pulse was issued and to the amplifier in the inter pulse intervals. The switches were made by opto-coupled field effect transistors, as these produced very little switching noise (no charge injection through a gate capacitance). Also, they had no galvanic connection between the switched signal and the control signal, which made them have very little effect on the common mode rejection properties of the amplifier. A more traditional way of obtaining this would be use a transformer coupling, but transformers are inherently bulky and would be difficult to use in an implantable device. The stimulator produced charge-balanced, current controlled pulses (1 mA, 0-255 μs pulse width). The PC controlled the stimulator and sampled and processed the amplified nerve signal. Clearly, the above-described embodiment is merely a laboratory test model, which for subsequent implementation would be miniaturized by incorporating the receiving and filtering means, the computing means as well as the stimulator in a small and lightweight apparatus which can be easily carried attached for example to the upper leg of a patient or carried in a belt. Further, the stimulating signals and the power for driving the electrodes 113 and thereto related circuitry would also be supplied to the implanted part of the system using a telemetric link as shown between the amplifier 114 and the receiver 116. Further, circuitry may be associated with the electrodes 113 and the external components of the system for coding and de-coding the signals as described above.

Figure 12:
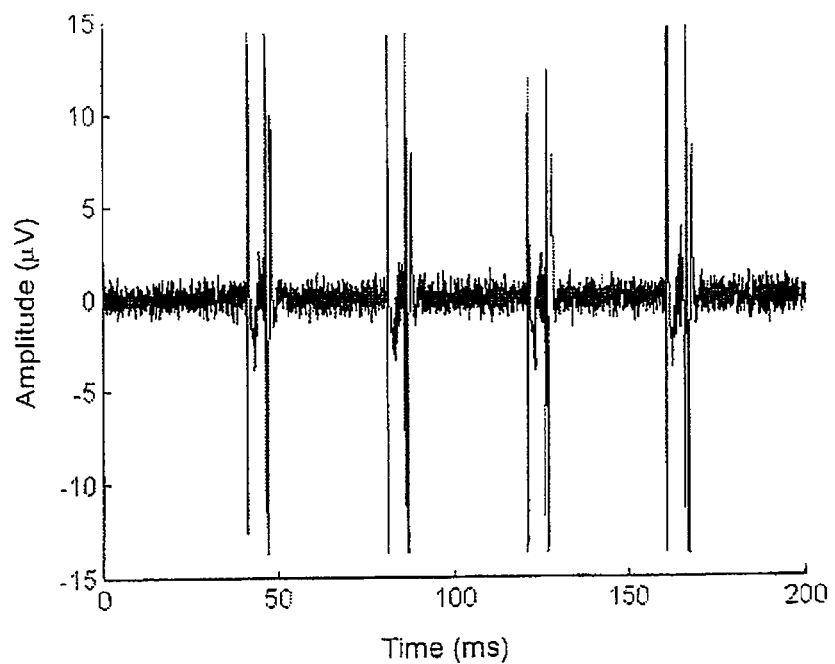
FIG. 12 shows a raw signal recorded during stimulation.

FIG. 12 shows an example of the raw signal recorded during stimulation. The combined stimulation artefacts and switching noise were short enough in duration (10 ms) to allow a sufficiently long window between them for recording of the nerve signal.

Figure 13:
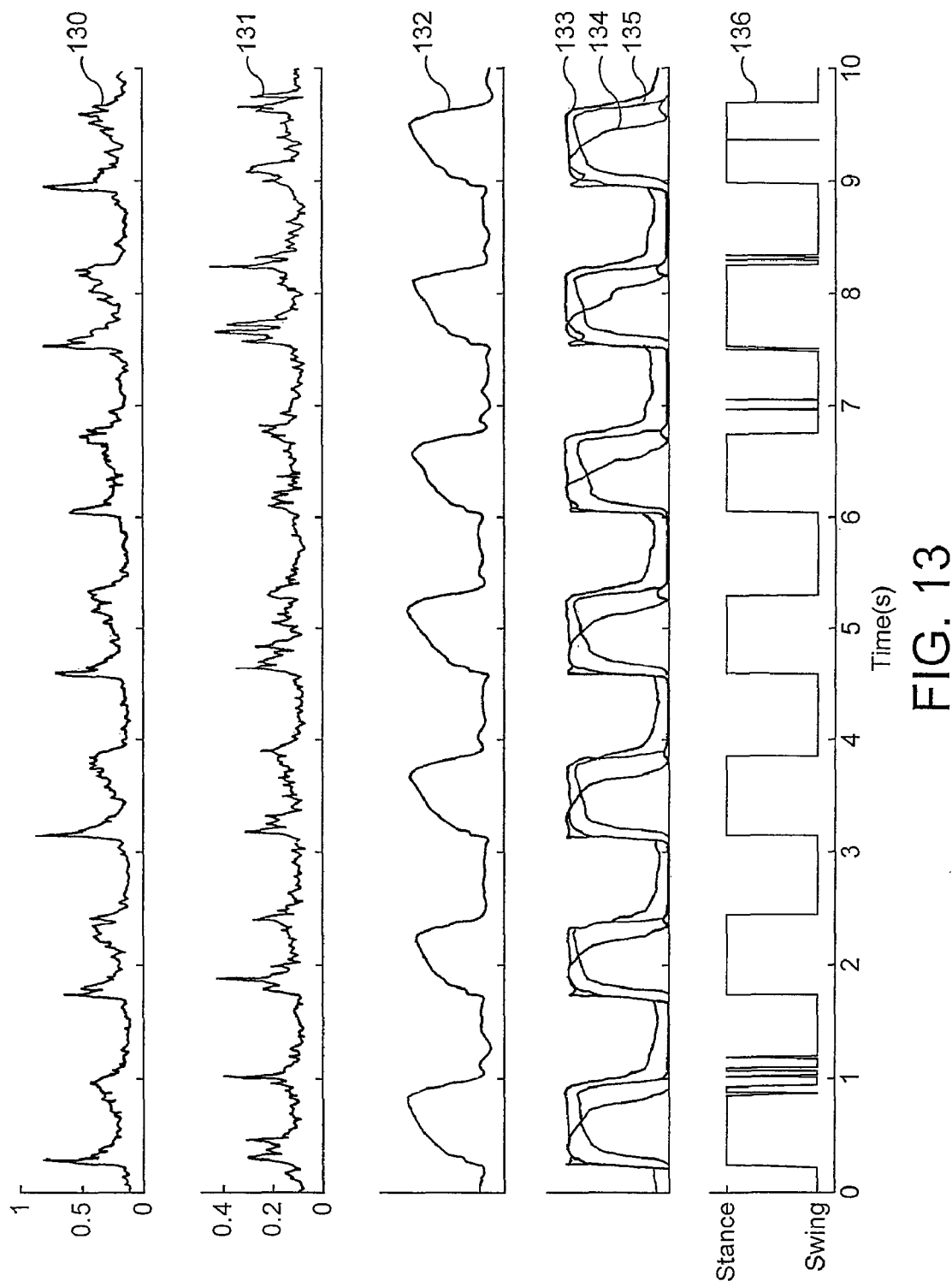
FIG. 13 shows data recorded from the peroneal nerve cuff during gait.

FIG. 13 shows data recorded from the peroneal nerve cuff during gait (without stimulation). Top trace is the rectified and bin-integrated sural nerve signal 130, which is included for comparison only. Second trace is the corresponding peroneal nerve signal 131. For reference are shown the ankle angle 132 (recorded with a Penny & Giles goniometer) and signals recorded from force sensitive resistors (FSR's) placed under the foot at the heel 134, and at the medial 135 and lateral 133 metatarsals.

It is clear that the peroneal nerve signal modulated in synchrony with the gait cycle and had features similar to the sural nerve signal. It was then investigated if the signal-processing algorithm for extracting a stimulator control signal could be applied on the peroneal nerve signal based on an adaptive logic network (ALN). This type of network is described in the literature, and consists of a number of so-called linear threshold units and a number of logic nodes [A. Kostov, B. J. Andrews, D. B. Popovic, R. B. Stein, W. W. Armstrong (1995) Machine learning in control of functional electrical stimulation systems for locomotion IEEE Trans. Biomedical Engineering, vol. 42, no. 6, pp. 541-551]. Due to the logic nature of the network it is very simple to implement in a portable device, such as the micro-controller described above. The last trace 136 in FIG. 13 shows the result of this. The network was trained on 50 seconds of plain gait and evaluated on another 50 seconds of plain gait. Comparing the target signal obtained from the FSR's with the output of the ALN yielded correct samples, which was as high as that obtained by using the sural nerve signal.

Figure 14:
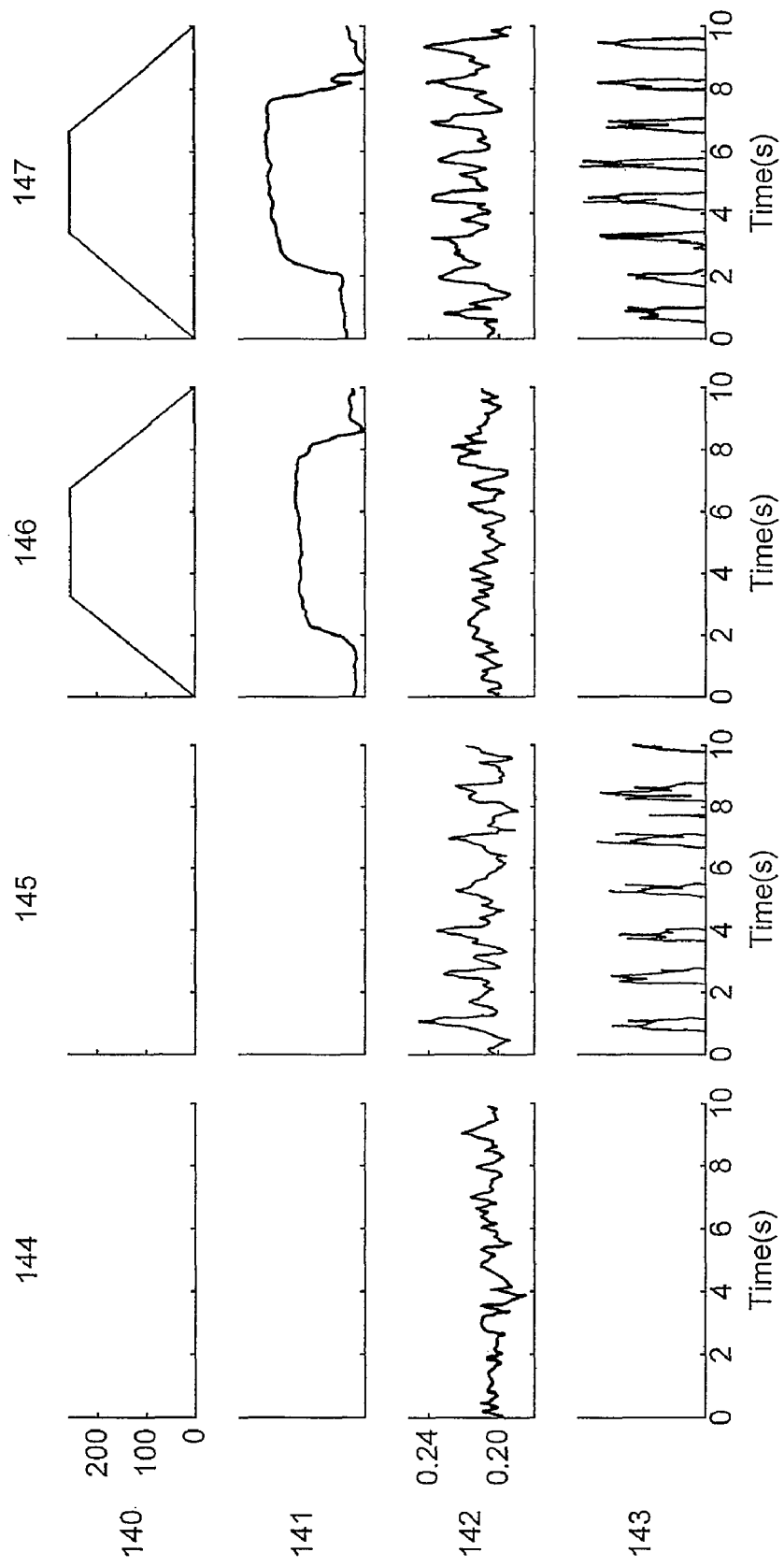
FIG. 14 shows results from stimulating and recording at the same time from the same cuff.

FIG. 14 shows results from stimulating and recording at the same time from the same cuff. The subject was sitting down. The circuit shown in FIG. 11 was connected to one set of electrodes in the peroneal cuff. The first row 140 shows the stimulation intensity (pulse width in microseconds, current=1 mA, frequency=25 Hz). Second row 141 shows the output from a force sensor (un-calibrated) held manually on the dorsum of the foot to give indication of the effect of the stimulation. Third row 142 shows the rectified and bin-integrated Peroneal nerve signal (in micro Volts) Fourth row 143 shows a touch sensor (un-calibrated) that was used for manually stroking the skin to give an indication of when sensory signals should be expected. The data in the first column 144 were recorded when was no stimulation and no touch of the skin. The recorded signal thus represented the background activity of the system. In the second column 145 the foot was touched within the cutaneous innervation area of the Peroneal nerve and the recorded nerve signal modulated correspondingly. In the third column 146 stimulation was applied through the cuff but the skin was not touched. This gave a small increase in the nerve signal corresponding to the movement of the toes caused by the change in stimulation intensity but no apparent change that could be related directly to the stimulation artefacts. In the fourth column 147 the Peroneal nerve was stimulated through the cuff and the skin was touched. It can be seen that it was still possible to get a clear nerve signal from the nerve that modulated in accordance to the touch of the skin, even when stimulating the same nerve with the same electrode.

CONCLUSIONS

It has been demonstrated that it is possible to stimulate a peripheral nerve and to record natural sensory information from this nerve via a single set of electrodes, multiplexed fast enough to be functionally concurrent. This may be very useful in a number of applications where natural sensory feedback can add performance to a neuroprosthesis.

It has further been demonstrated that it is possible to record gait-related information from the Peroneal nerve above the knee and use it to produce a control signal suitable for controlling a peroneal stimulator for correction of foot drop.

The invention claimed is:

1. Apparatus for producing a dorsiflexion of the foot of a patient, comprising:
    a combined sensing and stimulation electrode device having neurosense and stimulation electrode means capable of sensing a nerve signal from a peripheral nerve and stimulating peripheral motor nerve fibres, wherein said neurosense and stimulation electrode means are adapted to be implanted at a location on a single nerve above the knee of the patient through a single surgical incision;
    means for receiving and processing the nerve signals sensed in from said location of the patient above the knee of the patient to identify a signal indicative of the timing of heel strike and heel lift of the patient and for producing a control signal in response thereto, and
    means for operating said neurosense and stimulation electrode means in response to the control signal to produce a stimulation of the peripheral motor nerve fibres at said location of to produce dorsiflexion of the foot of the patient.

2. Apparatus as claimed in claim 1, wherein the neuro sense and stimulation electrode device comprise at least one combined sensing and stimulating electrode configured for arrangement on a single peripheral nerve.

3. Apparatus as claimed in claim 2, further comprising means for switching each combined sensing and stimulation electrode between a sensing state and a stimulating state.

4. Apparatus as claimed in claim 3, wherein the means for switching each combined sensing and stimulation electrode between a sensing state and a stimulating state comprises at least one opto-coupled field effect transistor.

5. Apparatus as claimed in claim 1, wherein the combined neurosense and stimulation electrode device comprises:
    at least one neurosense electrode configured for arrangement on a peripheral nerve for sensing a nerve signal from the peripheral nerve; and
    at least one stimulation electrode configured for arrangement on the same peripheral nerve for stimulating a peripheral motor nerve fibre.

6. Apparatus as claimed in claim 2 or claim 5, wherein one or more of said sensing, stimulating and combined sensing and stimulating electrodes are located in a single cuff and the cuff is configured for arrangement around a single peripheral nerve.

7. Apparatus as claimed in claim 6, wherein the peripheral nerve is the common peroneal nerve.

8. Apparatus as claimed in claim 6, wherein the peripheral nerve is the sciatic nerve.

9. Apparatus as claimed in claim 5, wherein one or more of said sensing electrodes are located in a first cuff and the first cuff is configured for arrangement around a first single peripheral nerve and one or more of said stimulating electrodes are located in a second cuff and the second cuff is configured for arrangement around a second single peripheral nerve adjacent the first peripheral nerve.

10. Apparatus as claimed in claim 9, wherein the first peripheral nerve is the tibial nerve and the second peripheral nerve is the common peroneal nerve.

11. Apparatus as claimed in claim 5, wherein one or more of said sensing, stimulating and combined sensing and stimulating electrodes are located in a single cuff and the cuff is configured for arrangement around a single peripheral nerve.

12. Apparatus as claimed in claim 1, further comprising implantable communication means for enabling communication between the operating means and a computer located external to a patient's body, said communication means being arranged to either one or both of receive and store programs for use by the operating means.

13. Apparatus as claimed in claim 1, the receiving and processing means comprising first and second receiving and processing means, wherein:
    the first receiving and processing means are arranged to process a signal received from the neurosense and stimulation electrode means and to provide a first serially coded signal for transmitting to said second receiving and processing means;
    the second receiving and processing means comprise means for receiving the first serially coded signal, identifying the signal indicative of the timing of heel strike and heel lift, providing a second serially coded control signal in response thereto and transmitting the second serially coded control signal to the operating means; and
    the operating means are configured to decode the second serially coded control signal and to provide a control signal for transmission to the neurosense and stimulation electrode means.

14. Apparatus as claimed in claim 13, wherein the first receiving and processing means and the operating means are housed in the same device.

15. Apparatus as claimed in claim 14, wherein the device housing the first receiving and processing means and the operating means is adapted to be implanted above the knee of a patient.

16. Apparatus as claimed in claim 14, wherein the device housing the first receiving and processing means and the operating means is adapted to be implanted in the thigh of a patient.

17. Apparatus as claimed in claim 14, further comprising a power source for powering the first receiving and processing means and the operating means, wherein the power source is a rechargeable battery located in the device housing the receiving and processing means and the operating means.

18. Apparatus as claimed in claim 17, wherein the rechargeable battery is inductively chargeable by a second power source located external to a patient's body.

19. Apparatus as claimed in claim 14, further comprising a power source for powering the first receiving and processing means and the operating means, wherein the power source is located external to a patient's body.

20. Apparatus as claimed in claim 13, wherein signals between the first receiving and processing means and the second receiving and processing means are transmitted cordlessly through a patient's skin.

21. Apparatus as claimed in claim 1, further comprising a power source for powering the operating means, wherein the power source is adapted to be implanted with the operating means.

22. Apparatus as claimed in claim 1, wherein said neurosense and stimulation electrode means are adapted to be implanted above the knee of a patient.

23. Apparatus as claimed in claim 13, wherein said neurosense and stimulation electrode means, first receiving and processing means and operating means are adapted to be implanted above the knee of a patient.

24. Apparatus as claimed in claim 13, wherein said neurosense and stimulation electrode means are adapted to be implanted above the knee of a patient and said first receiving and processing means and operating means are adapted to be implanted in the thigh of a patient.

* * * * *